United States Patent
Cagle et al.

(10) Patent No.: US 10,143,515 B2
(45) Date of Patent: Dec. 4, 2018

(54) DETACHABLE BAILOUT SHAFT FOR MOTORIZED RF DEVICE

(71) Applicant: Ethicon Endo-Surgery, LLC, Guaynabo, PR (US)

(72) Inventors: David J. Cagle, Cincinnati, OH (US); Catherine A. Corbett, Cincinnati, OH (US); Kevin M. Fiebig, Cincinnati, OH (US); Richard L. Leimbach, Cincinnati, OH (US); Jason R. Lesko, Cincinnati, OH (US); Rudolph H. Nobis, Mason, OH (US); Geoffrey S. Strobl, Williamsburg, OH (US); Brett E. Swensgard, West Chester, OH (US); Aaron C. Voegele, Loveland, OH (US)

(73) Assignee: Ethicon LLC, Guaynabo, PR (US)

(*) Notice: Subject to any disclaimer, the term of this patent is extended or adjusted under 35 U.S.C. 154(b) by 301 days.

(21) Appl. No.: 14/940,443

(22) Filed: Nov. 13, 2015

(65) Prior Publication Data

US 2017/0135749 A1    May 18, 2017

(51) Int. Cl.
| | |
|---|---|
| *A61B 18/14* | (2006.01) |
| *A61B 17/295* | (2006.01) |
| A61B 18/00 | (2006.01) |
| A61B 17/00 | (2006.01) |
| F16H 19/04 | (2006.01) |
| F16H 25/20 | (2006.01) |
| F16H 1/14 | (2006.01) |
| A61B 17/29 | (2006.01) |

(52) U.S. Cl.
CPC ........ *A61B 18/1445* (2013.01); *A61B 17/295* (2013.01); *A61B 2017/00398* (2013.01); *A61B 2017/2923* (2013.01); *A61B 2018/00601* (2013.01); *A61B 2018/1452* (2013.01); *F16H 1/14* (2013.01); *F16H 19/04* (2013.01); *F16H 25/20* (2013.01); *F16H 2025/2093* (2013.01)

(58) Field of Classification Search
CPC .. A61B 2017/00398; A61B 2018/1452; A61B 2017/2923; A61B 18/1445; A61B 17/295; A61B 2018/00601; F16H 1/14; F16H 2025/2093; F16H 19/04; F16H 25/20
See application file for complete search history.

(56) References Cited

U.S. PATENT DOCUMENTS

| | | | |
|---|---|---|---|
| 2009/0202387 A1 | 8/2009 | Dlugos, Jr. et al. | |
| 2012/0116388 A1* | 5/2012 | Houser | A61B 17/00234 606/41 |

* cited by examiner

*Primary Examiner* — Jonathan Miles
*Assistant Examiner* — George J Ulsh
(74) *Attorney, Agent, or Firm* — Mintz Levin Cohn Ferris Glovsky and Popeo, P.C.

(57) ABSTRACT

Methods and devices are provided for retracting a cutting assembly in the event of a failure on a motorized electrosurgical device. For example, a surgical device is provided with a handle that has an elongate shaft assembly with first and second jaws for engaging tissue. A cutting assembly is included in the surgical device that cuts tissue engaged between the first and second jaws. The surgical device also includes a drive shaft that extends from the handle through the elongate shaft and moves the cutting assembly relative to the first and second jaws, and a motorized gear assembly that causes movement of the drive shaft. In an exemplary embodiment, the elongate shaft assembly is detachable from the handle such that, when detached, the drive shaft can be manually retracted relative to the elongate shaft to retract the cutting assembly from to the first and second jaws.

18 Claims, 7 Drawing Sheets

DETACHABLE BAILOUT SHAFT FOR MOTORIZED RF DEVICE

FIELD

Methods and devices are provided for retracting a cutting assembly in the event of a failure on a motorized electrosurgical device.

BACKGROUND

Endoscopic surgical instruments are often preferred over traditional open surgical devices since a smaller incision associated with endoscopic surgical techniques tends to reduce the post-operative recovery time and complications. Consequently, significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, stapler, clip applier, access device, drug/gene therapy delivery device, and energy device using ultrasound, RF, laser, etc.).

Endoscopic devices are passed through an access port, such as a trocar, to allow the distal end effector to engage tissue within a body cavity of a patient. With powered devices, any problems that occur may prevent removal of the device through the access port. For example, in the event the end effector becomes jammed during a firing stroke or the device otherwise fails, the end effector cannot be removed because tissue is engaged between the jaws. The surgeon may be forced to open up the patient and cut the instrument out of the patient, potentially causing serious harm to the patient.

Accordingly, there remains a need for methods and devices for retracting a cutting assembly in the event of a failure on a motorized electrosurgical device.

SUMMARY

Various methods and devices are provided for retracting a cutting assembly in the event of a failure on a motorized electrosurgical device.

In one aspect, a surgical device is provided that includes an elongate shaft assembly and a handle. The elongate shaft assembly has first and second jaws at a distal end thereof for engaging tissue, and has a cutting assembly extending therethrough for cutting tissue engaged between the first and second jaws. The handle has a motorized gear assembly coupled to the drive shaft for causing movement of the drive shaft. The handle includes a mechanism for detaching the elongate shaft assembly from the handle such that the drive shaft can be withdrawn distally from the handle to cause the drive shaft to retract the cutting assembly from the first and second jaws.

The surgical device can vary in any number of ways. For example, the device can include at least one living hinge that can be depressed to at least partially detach the elongate shaft assembly. As another example, the handle can include a button that, when actuated, allows the elongate shaft assembly to be at least partially detached from the handle. In another example, the drive shaft can be coupled to the handle by a bailout clip removably disposed in the handle with removal of the bailout clip allowing the elongate shaft assembly to be at least partially detached from the handle. In still another example, the elongate shaft assembly can includes a jaw closure shaft configured to move the first and second jaws between an opened position and a closed position while the jaw closure shaft is coupled to the handle by a plurality of ball bearings, and the ball bearings are configured to disengage from the jaw closure shaft to allow the jaw closure shaft to detach from the handle. In furtherance of that example, the device can also include at least one living hinge that can be depressed to at least partially detach the elongate shaft assembly. The handle can further include a button that, when actuated, allows the elongate shaft assembly to be at least partially detached from the handle. The elongated shaft assembly can additionally be coupled to the handle by a bailout clip removably disposed in the handle, wherein removal of the bailout clip allows the elongate shaft assembly to be at least partially detached from the handle.

In another aspect, a surgical device is provided that includes a handle, an elongate shaft, a cutting assembly, a drive shaft, and a motorized gear assembly. The elongate shaft assembly extends distally from the handle, and the elongate shaft assembly has first and second jaws at a distal end thereof for engaging tissue therebetween. The cutting assembly is movable relative to the first and second jaws so as to cut tissue engaged between the first and second jaws, and the drive shaft extends from the handle through the elongate shaft and is coupled to the cutting assembly for moving the cutting assembly relative to the first and second jaws. The motorized gear assembly is coupled to the drive shaft and is configured to cause movement of the drive shaft. The elongate shaft assembly is at least partially detachable from the handle such that, when detached, the drive shaft can be manually retracted relative to the elongate shaft to move the cutting assembly relative to the first and second jaws.

The surgical device can vary in any number of ways. For example, the device can include at least one living hinge that can be depressed to at least partially detach the elongate shaft assembly. As another example, the handle can include a button that, when activated, allows the elongate shaft to be at least partially detached from the handle. In another example, the elongate shaft assembly can be coupled to the handle by a bailout clip removably disposed in the handle with removal of the bailout clip allowing the elongate shaft to be at least partially detached from the handle. In another embodiment, the elongate shaft assembly can include a jaw closure shaft configured to move the first and second jaws between an opened position and a closed position with the jaw closure shaft being coupled to the handle by a plurality of ball bearings, and the ball bearings are configured to disengage from the jaw closure shaft to allow the jaw closure shaft to detach from the handle. In furtherance of that example, the device can also include at least one living hinge that can be depressed to at least partially detach the elongate shaft assembly. The handle can further include a button that, when actuated, allows the elongate shaft assembly to be at least partially detached from the handle. The elongated shaft assembly can additionally be coupled to the handle by a bailout clip removably disposed in the handle, wherein removal of the bailout clip allows the elongate shaft assembly to be at least partially detached from the handle.

In another aspect, a method for cutting tissue is provided that includes engaging tissue between first and second jaws on an elongate shaft of a surgical device. The method also includes actuating a drive mechanism to distally advance a cutting assembly along the first and second jaws and thereby at least partially cut the tissue engaged between the first and second jaws. The method further includes detaching the elongate shaft from a handle of the surgical device and moving the elongate shaft distally relative to the handle to cause a drive shaft coupled to the cutting assembly to proximally retract the cutting assembly relative to the first and second jaws.

The method can vary in any number of ways. For example, detaching the elongate shaft from the surgical device can include depressing at least one living hinge to release the elongate shaft assembly from the handle. As another example, detaching the elongate shaft can include depressing a button on the handle to disengage the elongate shaft from the handle. In another example, detaching the elongate shaft can include activating a mechanism to release a ball bearing from engagement with a jaw closure shaft such that the jaw closure shaft is detached from the handle. In yet another example, detaching the elongate shaft from the handle can include removing a bailout clip from the handle to release the elongate shaft.

BRIEF DESCRIPTION OF DRAWINGS

The embodiments described above will be more fully understood from the following detailed description taken in conjunction with the accompanying drawings. The drawings are not intended to be drawn to scale. For purposes of clarity, not every component may be labeled in every drawing. In the drawings.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various exemplary methods and devices are provided for retracting a cutting assembly in the event of a failure on a motorized electrosurgical device. In particular, methods and devices are provided for disengaging an elongate shaft on a motorized electrosurgical device so as to allow a drive shaft and cutting assembly to be manually retracted.

Figure 1:
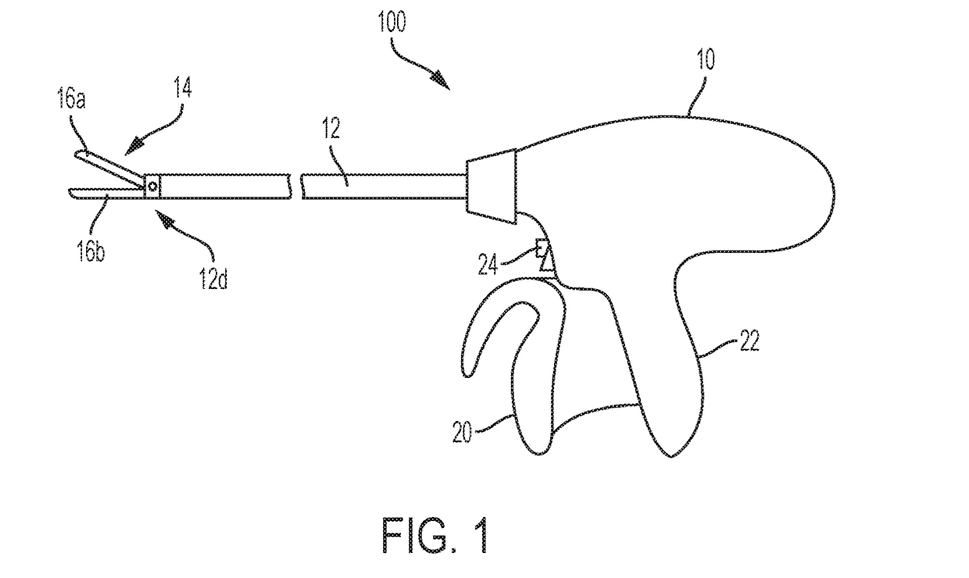
FIG. 1 is a side view illustration of one embodiment of a powered surgical device.

FIG. 1 illustrates one embodiment of a surgical device configured to grasp and cut tissue. As shown, the illustrated surgical device 100 generally includes a proximal handle portion 10, a shaft portion 12, and an end effector 14 for grasping tissue. The proximal handle portion 10 can be any type of pistol-grip, scissor grip, pencil-grip, or other type of handle known in the art that is configured to carry various actuators, such as actuator levers, knobs, triggers, or sliders, for actuating various functions such as rotating, articulating, approximating, and/or firing the end effector 14. In the illustrated embodiment, the proximal handle portion 10 includes a stationary grip 22 and a closure grip 20 that is movable toward and away from the stationary grip 22 to open and close jaws of the end effector 14. The shaft portion 12 extends distally from the proximal handle portion and has a lumen (not shown) extending therethrough for carrying mechanisms for actuating the end effector 14.

The end effector can have a variety of sizes, shapes, and configurations. As shown in FIG. 1, the end effector 14 includes a first upper jaw 16a and a second lower jaw 16b disposed at a distal end 12d of the shaft portion 12. The jaws 16a, 16b are moveable between an open position in which the jaws 16a, 16b are spaced a distance apart, and a closed position in which the jaws 16a, 16b are moved toward one another and are substantially opposed. When the jaws 16a, 16b are in the closed position, a longitudinal axis of the upper jaw 16a can be substantially parallel to a longitudinal axis of the lower jaw 16b and the jaws 16a, 16b can be in direct contact for engaging tissue therebetween. In the illustrated embodiment, the upper jaw 16a pivots relative to the shaft portion 12 and relative to the lower jaw 16b while the lower jaw 16b remains stationary. While the illustrated jaws 16a, 16b have a substantially elongate and straight shape, a person skilled in the art will appreciate that one or both of the jaws 16a, 16b can be in various directions. The jaws 16a, 16b can have any suitable axial length for engaging tissue, and the length can be selected based on the targeted anatomical structure for transection and/or sealing.

As indicated above, the surgical device 100 can have a closure actuator that can be configured to open and close the jaws 16a, 16b of the end effector 14. Manipulation of the closure actuator can pivot or otherwise move the jaws relative to one another such that the jaws can engage tissue, move anatomical structures, or perform other surgical functions. The closure actuator can have various sizes, shapes, and configurations, but in the illustrated embodiment the closure actuator includes the closure grip 20 and the stationary grip 22. The closure grip 20 can be moveable toward and away from stationary grip 22, such as via pivoting. In particular, the closure grip 20 can have a first position in which it is angularly offset and spaced apart from the stationary grip 22 and the jaws 16a, 16b of the end effector 14 are open. The closure grip 20 can have a second position where it is positioned adjacent to, or substantially in contact with, the stationary grip 22 and the jaws 16a, 16b of the end effector 14 can engage tissue and apply a force to tissue disposed therebetween. The closure grip 20 can be biased to the first open position with the jaws 16a, 16b of the end effector 14 being open, as shown in FIG. 1. The closure grip 20 can move the jaws 16a, 16b between the open and closed positions using manual or powered components. For example, in manually actuated embodiments, the closure grip 20 can be coupled to gears that interact with a rack disposed within the handle. Manual movement of the closure grip 20 toward the stationary grip 22 can move the rack either proximally or distally relative to the end effector 14 to either pull or push the jaws 16a, 16b closed. In other embodiments, the drive shaft can include or be coupled to a drive screw which can be moved proximally by a drive nut that is rotated by a series of gears. In powered embodiments, a motor can be disposed in the proximal handle portion 10 and manual movement of the closure grip 20 can cause a control signal to be sent to the motor, which can interact with various gears or other components to cause the jaws 16a, 16b to close. The closure grip 20 can interact with one or more locking features (not shown) configured to lock the closure grip 20 relative to the stationary handle 22. For example, the locking feature can automatically engage when the closure grip 20 substantially contacts the stationary handle 22 or the locking feature can automatically engage at each position the closure grip 20 is pivoted through, such as via ratcheting.

In certain embodiments the surgical device can also have a second actuator, such as actuator 24, that can be separate from the closure actuator 20. The second actuator can be configured to advance a cutting assembly, apply energy to tissue, or both, and is referred to herein as a "firing actuator." The firing actuator 24 can have various sizes, shapes, and configurations, but in the illustrated embodiment it is in the form of a button or trigger that can be depressed by a user. In another embodiment, the firing actuator 24 can be in the form of a switch, lever, etc., that can be slid, pivoted, or otherwise moved by a user. Depressing or pivoting the actuator can activate various elements in the device, and can cause a cutting assembly to advance through the end effector and/or cause energy to be delivered to the jaws. For example, depressing or pivoting the firing actuator can cause a cutting assembly to advance distally and/or retract proximally relative to the jaws 16a, 16b. More specifically, the firing actuator can be in electrical communication with a motor disposed in the proximal handle portion 10. The motor can be operatively coupled to the cutting assembly using known components, such as one or more gears and a rack or drive screw.

Figure 2:
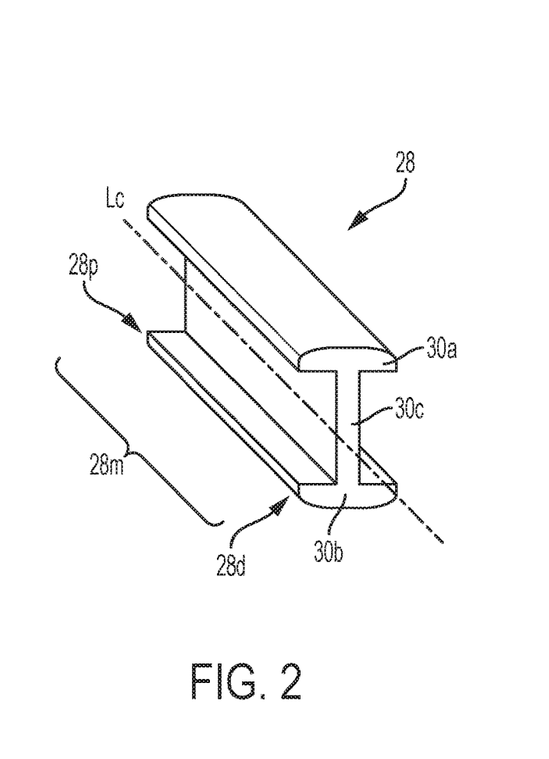
FIG. 2 is a perspective view illustration of a compression member of the powered surgical device of FIG. 1.

The cutting assembly can be configured to transect tissue captured between the jaws, and it can be sized and shaped to transect or cut various thicknesses and types of tissue. In one exemplary embodiment, as shown in FIG. 2, the cutting assembly can include an I-beam compression member 28 that travels through slots formed in each jaw to pull the jaws into a parallel orientation and to compress tissue therebetween. The compression member 28 can include a cutting element (not shown) positioned at the distal end 28d thereof and formed on a connecting portion 30c of the compression member 28. In some embodiments, the cutting element can be integrally formed with the distal end 28d of the compression member 28. The cutting element can have a sharp or serrated edge configured to transect the tissue. In some embodiments, the cutting element can be recessed relative to distal ends of upper and lower flanges 30a, 30b of the I-beam compression member 28 so that compression occurs prior to transecting or cutting of the tissue. In another embodiment, the cutting element can include a shaft having a knife blade that is not attached to a compression member such that the cutting assembly can advance and retract relative to the jaws without applying compression to the tissue.

Figure 3:
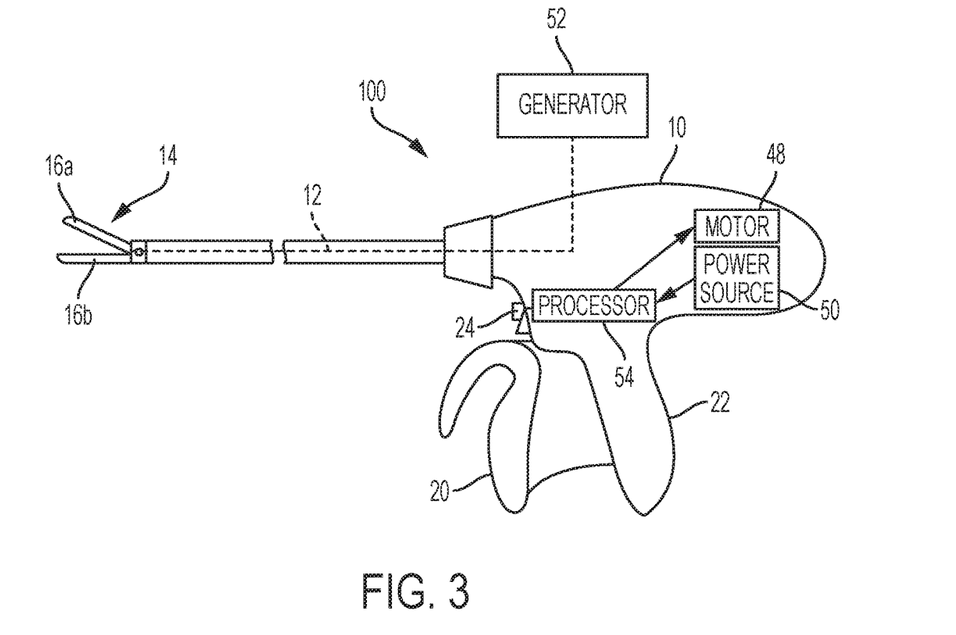
FIG. 3 is a side view illustration of the powered surgical device of FIG. 1.

As shown in FIG. 3, the handle portion 10 of the surgical device 100 can include components for operating the device, such as a motor 48, a power source 50, a generator 52, and a processor 54, as well as various sensors (not shown). The device 100 can also include various components for delivering energy, such as radiofrequency or ultrasound energy, to tissue, and these components can be disposed at various locations in the device 100, such as in the proximal handle portion 10 and/or in the jaws 16a, 16b. The firing actuator 24 can be coupled to the processor 54, and the processor 54 can be coupled to the motor 58, the power source 50, and/or the generator 52 (as well as any sensors provided). Firing the actuator 24 sends a signal to the processor 54, which can cause the power source 50 to provide power to the motor 48 through the processor 54. The motor 48 can drive the cutting assembly, and the processor 54 can control a speed and a direction of the motor, which in turn alters a speed and a direction of the cutting assembly.

The generator 52 can be a separate unit that is electrically connected to the surgical device 100 to decrease the size and weight of the surgical device 100, and it can be operatively coupled to an actuator on the surgical device so that the device is configured to apply energy to tissue engaged by the end effector when the actuator is activated. The generator can be operably coupled to the firing actuator 24 or the generator can be coupled to a second actuator. The generator can be any suitable generator known in the art, such as an RF generator or an ultrasound generator. A lumen (not shown) of the shaft portion 12 can carry electrical leads or wires that can deliver electrical energy to components of the end effector 14. The generator 52 can be coupled to the power source 50, such as a battery disposed in the proximal handle portion 10 or it can be coupled to an external power source, such as an electrical outlet.

Figure 4:
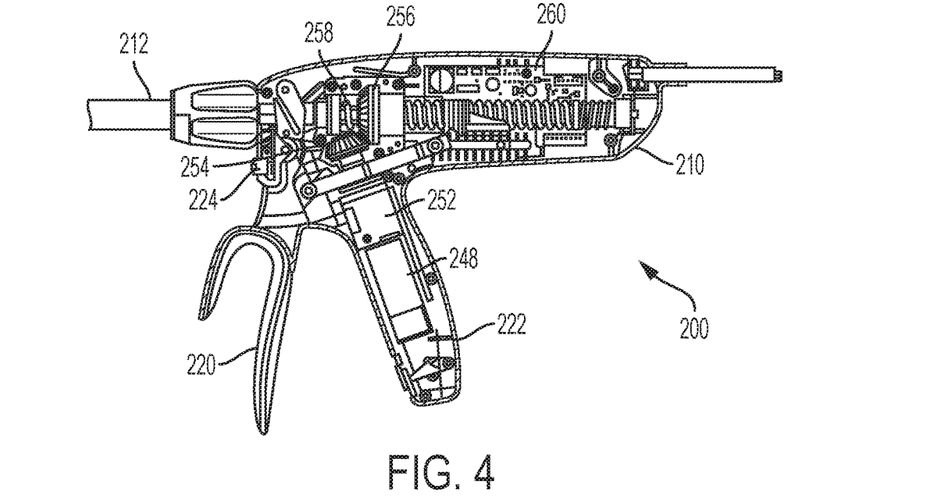
FIG. 4 is a side cutaway view of another embodiment of a powered surgical device.

FIG. 4 illustrates one exemplary configuration of a surgical device 200 having components for operating the device. The surgical device 200 can generally be configured and used similar to the surgical device 100 of FIGS. 1-3. As seen in FIG. 4, the surgical device 200 has a shaft portion 212, and a proximal handle portion 210 including a closure grip 220 and a stationary grip 222. The surgical device 200 has a firing actuator 224 that is configured to advance distally and/or retract proximally a cutting assembly through an end effector (not shown) positioned on a distal end of the shaft portion 212. The firing actuator 224 is a button that can be depressed by a user. The firing actuator 224 is coupled to and in communication with a processor 260, which can include a circuit board and/or a controller. The processor 260 can in turn be in communication with a motor 248, a power source such as a battery, and/or a generator. The motor 248 is disposed in the proximal handle portion 210, and it can be operatively coupled to a gear box 252, which is operably coupled to a motor bevel gear 254. The motor bevel gear 254 is operably coupled in turn to a drive bevel gear 256, which is operably coupled to a drive shaft 258. Activation of the firing actuator 224 can thus provide a signal to the processor 260. The processor 260 can cause power to be delivered from the power source to the motor 248, which rotates the gear box 252. The gear box 252 causes the motor bevel gear 254 to rotate, which engages with and rotates the drive bevel gear 256, which drives the drive shaft 258 distally or proximally. Upon rotation of the drive bevel gear 256, the drive shaft 258 can be driven distally or proximally through known means, such as a thread along the drive shaft 258. Distal movement of the drive shaft 258 advances the cutting assembly distally through an end effector. Proximal movement of the drive shaft 258 retracts the cutting assembly proximally from the end effector. A person skilled in the art will appreciate that the drive shaft can be advanced and retracted using a number of different techniques, such as a rack system, one or more linkages, a ball bearing and nut system, a bevel and spur gear system, etc.

As indicated above, the surgical device 200 has a generator (not shown) that is operatively coupled to an actuator on the surgical device 200 so that the device 200 is configured to apply energy to tissue engaged by the end effector when the actuator is activated. The generator can be operably coupled to the firing actuator 224 or the generator can be coupled to a second actuator. The generator can be any suitable generator known in the art, such as an RF generator or an ultrasound generator. A lumen (not shown) of the shaft portion 212 can carry electrical leads or wires that can deliver electrical energy to components of the end effector.

Under normal operation of a surgical device as described above, power can be supplied from a power source, e.g., the battery, through a processor to a motor, resulting in distal or proximal movement of a cutting assembly through an end effector positioned on a distal end of the surgical device. In certain instances, the surgical device may fail to successfully complete a cutting stroke, for example if the device jams during cutting because of thick tissue or if a power failure occurs. Removing the surgical device from a patient before retracting the cutting assembly may cause significant harm to the patient, though. If the surgical device malfunctions during a firing stroke, i.e., prior to full advancement and full retraction of the cutting assembly, a surgeon may be required to retract the cutting assembly from the jaws of the end effector to relieve compression on the tissue. As another example, a cutting assembly that also applies compression can potentially hold the jaws clamped on tissue if a failure occurs. In such an occurrence, the surgeon might be required to cut out the surgical device. Accordingly, a bailout mechanism is provided that can allow retraction of the cutting assembly in the event of a malfunction.

In general, a surgical device can be provided with a handle that has an elongate shaft extending distally therefrom with first and second jaws at a distal end for engaging tissue. A cutting assembly can be configured to move relative to the first and second jaws to cut tissue engaged between the two jaws. A drive shaft can extend from the handle through the elongate shaft and can be coupled to the cutting assembly so that the drive shaft can move the cutting assembly relative to the first and second jaws. A motorized gear assembly can be coupled to the drive shaft and can be configured to cause movement of the drive shaft. The elongate shaft can be detachable from the handle such that, when detached, the drive shaft can be manually retracted relative to the elongate shaft to move the cutting assembly relative to the first and second jaws. The surgical device can thus have a bailout mechanism in which the elongate shaft is detached and the drive shaft and the cutting assembly can be manually retracted. Under normal operations, the motorized gear assembly can drive the drive shaft to cause the cutting assembly to move distally and proximally relative to the first and second jaws, thus allowing for a motorized advancement and retraction of the cutting assembly relative to the first and second jaws. When retracted, the first and second jaws can open to release tissue engaged there between, and a surgeon can subsequently withdraw the surgical device from a patient. The bailout mechanism may allow a surgeon to rapidly remove the surgical device during any emergency situation, for example if there is a power failure or the jaws and the cutting assembly jam, while minimizing any harm to the patient. Manual bailout of the cutting assembly in the form of detaching the elongate shaft and manually withdrawing the drive shaft and the cutting assembly may also be fast and less prone to continued device errors than other mechanisms, ensuring a safe retraction during a potentially high-stress situation in which the surgeon is attempting to monitor the patient and safely remove the device at the same time.

Figure 5:
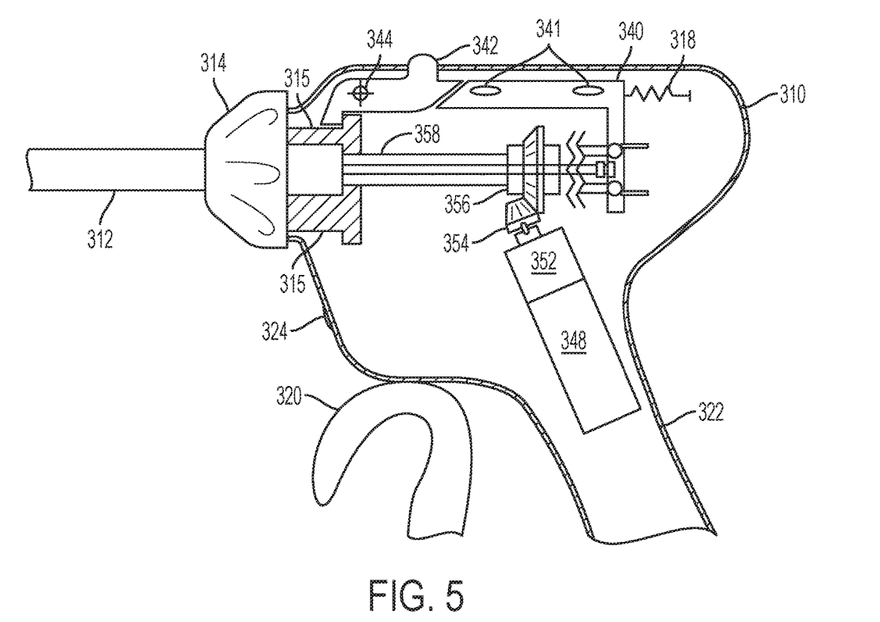
FIG. 5 is a side, partially cutaway view of another embodiment of a powered surgical device.
Figure 6:
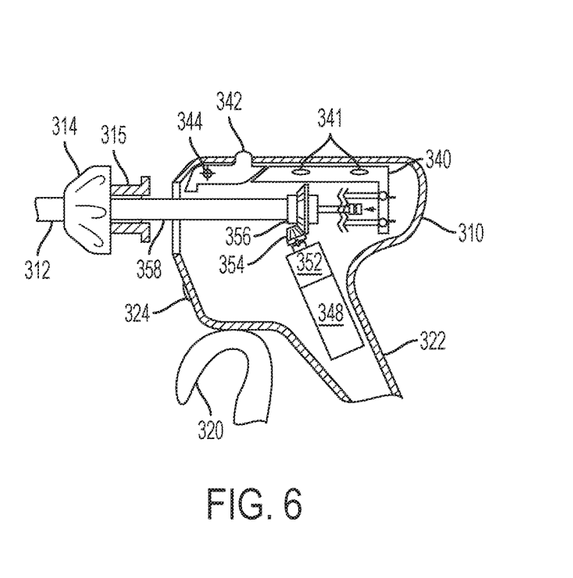
FIG. 6 is side, partially cutaway view of the powered surgical device of FIG. 5 during a bailout operation.

FIGS. 5-6 illustrate one embodiment of a surgical device 300 having a bailout mechanism. The surgical device 300 can generally be configured and used similar to the surgical devices 100, 200 of FIGS. 1-4. Surgical device 300 has a proximal handle portion 310 including a stationary grip 322. The surgical device 300 has a shaft portion 312 coupled to a rotator 314 that is rotatable relative to the handle for rotating the shaft. The device also includes a closure grip 320, and a firing actuator 324 that can be configured to advance distally and/or retract proximally a cutting assembly through an end effector (not shown) positioned on a distal end of the shaft portion 312. The closure grip 320 is effective to move jaws of the end effector between open and closed positions. The firing actuator 324 is connected to and in communication with a processor (not shown) within the proximal handle portion 310. The processor is in communication with a motor 348 and a power source (not shown) such as a battery. The motor 348 is operably coupled to a gear box 352 and is disposed in the proximal handle portion 310. The motor 348 and the gear box 352 are operatively coupled to a motor bevel gear 354 that is operably coupled (directly or indirectly) to a drive bevel gear 356, which in turn moves a drive shaft 358 proximally or distally.

Figure 5A:
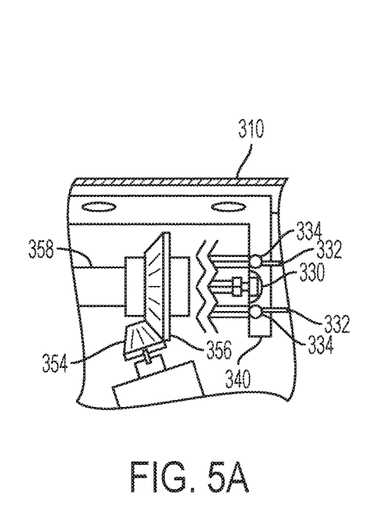
FIG. 5A is an enlarged side, partially cutaway view of part of the power surgical device of FIG. 5.

In this embodiment, a jaw closure shaft 330, which operates to open and close the jaws on the distal end of the shaft portion 312 upon operation of the closure grip 320, engages with a ball coupler 332 and balls 334 (as seen in FIG. 5A). The jaw closure shaft 330 extends with the drive shaft 358 through the shaft portion 312. The ball coupler 332 surrounds the jaw closure shaft 330 and is coupled to the proximal handle portion 310. The ball coupler 332 engages the jaw closure shaft 330 through the balls 334. The balls 334 are positioned in openings 336 on the ball coupler 332 and engage with corresponding openings or detents 338 on the jaw closure shaft 330. A horizontal portion of a slide 340 extends along a top surface of the proximal handle portion 310 and is configured to slide distally and proximally along one or more slide points 341. A vertical portion located at a proximal end of the slide 340 extends around the jaw closure shaft 330 and the ball coupler 332 in the form of a cylinder. The cylindrical end of the slide 340 is configured to apply a radially-inward compression force on the balls 334 to keep the balls 334 engaged with the openings 338 on the jaw closure shaft 338. Because the balls 334 also pass through the openings 336 on the ball coupler 332, the ball coupler 332 is maintained in engagement with the jaw closure shaft 330 as long as compression force keeps the balls 334 engaged with the openings 338 on the jaw closure tube 330. A spring 318 is coupled between a proximal wall of the proximal handle portion 310 and a proximal end of the slide 340 and acts to bias the slide 340 distally, maintaining the slide 340 around the balls 334 to thereby maintain the ball coupler 332 and the jaw closure shaft 330 in engagement. A circular flange 315 extends from the rotator 314 and acts to couple the rotator 314 to the proximal handle portion 310. A lever 342 extends externally from the proximal handle portion 310 and is accessible on a top surface of the proximal handle portion 310 and pivots about a pivot point 344. The distal end of the lever 342 engages the flange 315 and a proximal end of the lever 342 contacts the slide 340 when the lever 340 is depressed.

When the device is under a normal operation, the lever 340 maintains the flange 315 in engagement with the shaft, which keeps the rotator 314 engaged with the proximal handle 310, as seen in FIG. 5. The spring 318 biases the slide 340 distally to keep the ball coupler 332 engaged with the jaw closure shaft 330 through interaction of the balls 334. The jaws can be opened and closed upon operation of the closure grip 320. Techniques for advancing the closure shaft in response to engagement of the closure grip are known in the art. Actuation of the firing actuator 324 sends a signal to the processor, which drives the motor 348 by providing power to the motor 348 from the power source. The motor 348 drives the gear box 352, which drives the motor bevel gear 354, which drives the drive bevel gear 356. The drive bevel gear 356 will rotate, causing the drive shaft 358 to advance and retract with the cutting assembly.

If a bailout operation of the cutting assembly is required, the lever 342 can be depressed. The lever 342 rotates about pivot point 344, causing the distal end of the lever 342 to move away and disengage from the flange 315 and causing the proximal end of the lever 342 to press the slide 340. Disengaging the flange 315 results in the shaft portion 312, and the rotator 314 being free to move distally away from and separate from the proximal handle portion 310. Pressing the slide 340 causes proximal motion of the slide 340 upon overcoming the spring bias of spring 318, and will cause the slide 340 to move proximally relative to the ball coupler 332. Proximal motion of the slide 340 allows the balls 334 to move radially outward and disengage from the jaw closure shaft 330, releasing the balls 334 freely into the proximal handle portion 310 and releasing the jaw closure shaft 330 such that the jaws are freely openable and closable and can no longer be opened or closed upon operation of the closure grip 320. The drive shaft 358 with the cutting assembly is still engaged with the proximal handle portion 310. The shaft portion 312 can be pulled distally away from the proximal handle portion 310. Because the drive shaft 358 is fixed to the proximal handle portion 310, the cutting assembly attached to the drive shaft 358 is pulled out of the jaws. In other words, the jaws are pulled distally relative to the cutting assembly.

The surgical device 300 cannot be reused after operating the lever 342 and retracting the cutting assembly. In other variations, the device can be reusable by re-engaging the shaft portion, the rotator, and the flanges with the proximal body portion. In such an example, the balls could be configured to move out of engagement with the jaw closure shaft while still engaging the ball coupler, for example by positioning detents on the slider to engage and retain the balls, allowing the device to be reset to normal operation upon realigning the jaw closure shaft with the ball coupler. In this embodiment, the balls 334 and the ball coupler 332 are used to engage the jaw closure shaft 330 with the proximal handle portion 310, but any coupling mechanism can be used, such as a clip, a hook, etc.

Figure 7:
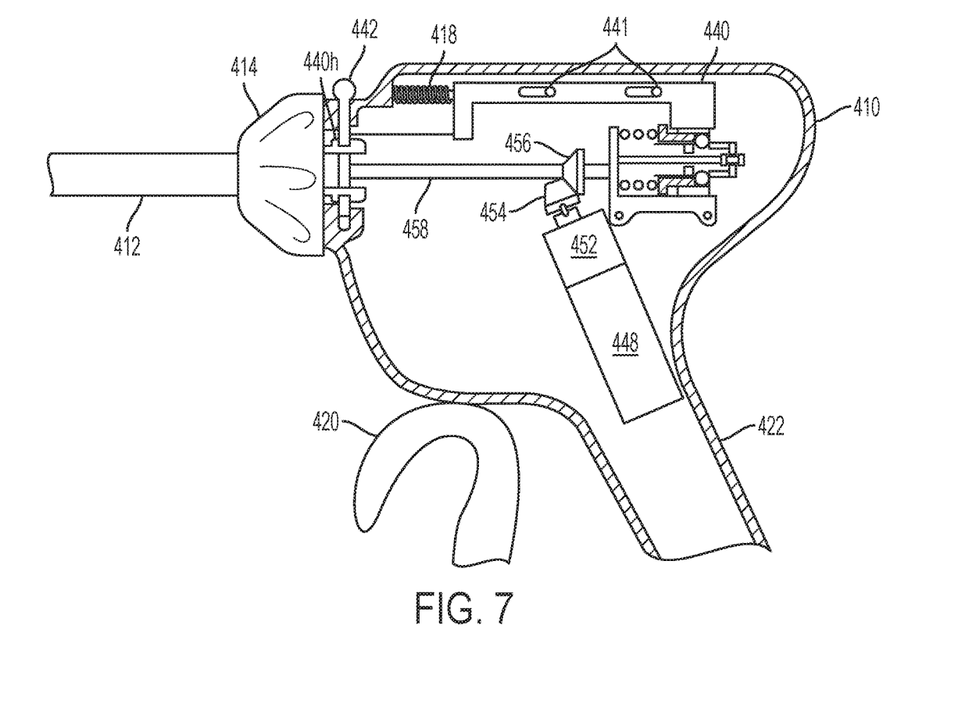
FIG. 7 is a side, partially cutaway view of another embodiment of a powered surgical device.
Figure 8:
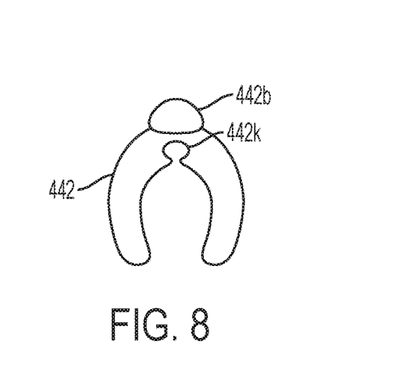
FIG. 8 is a side view of an embodiment of a clip from the surgical device of FIG. 7.

FIGS. 7-8 illustrate another embodiment of a surgical device 400 having a bailout mechanism. The surgical device 400 can generally be configured and used similar to the surgical devices 100, 200 of FIGS. 1-4. Surgical device 400 has a proximal handle portion 410 including a stationary grip 422. The surgical device 400 has a shaft portion 412 coupled to a rotator 414, a closure grip 420, and a firing actuator 424 that can be configured to advance distally and/or retract proximally a cutting assembly through an end effector (not shown) positioned on a distal end of the shaft portion 412. The closure grip 420 is effective to move jaws of the end effector between open and closed positions. The firing actuator 424 is connected to and in communication with a processor (not shown) within the proximal handle portion 410. The processor is in communication with a motor 448 and a power source (not shown) such as a battery. The motor 448 is operably coupled to a gear box 452 and is disposed in the proximal handle portion 410. The motor 448 and the gear box 452 are operatively coupled to a motor bevel gear 454 that is operably coupled (directly or indirectly) to a drive bevel gear 456, which in turn moves a drive shaft 458 proximally or distally.

Figure 7A:
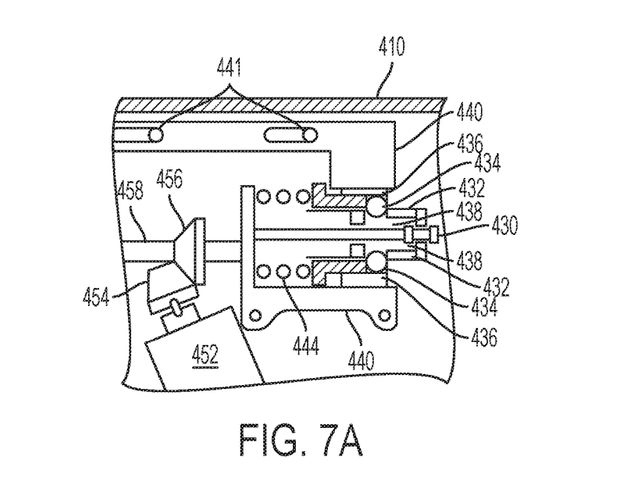
FIG. 7A is an enlarged side, partially cutaway view of part of the power surgical device of FIG. 7.

In this embodiment, a jaw closure shaft 430, which operates to open and close the jaws on the distal end of the shaft portion 412, engages with a ball coupler 432 and balls 434 (as seen in FIG. 7A). The jaw closure shaft 430 extends with the drive shaft 458 through the shaft portion 412. The ball coupler 432 surrounds the jaw closure shaft 430 and is coupled to the proximal handle portion 410. The ball coupler 432 engages the jaw closure shaft 430 through the balls 434. The balls 434 are positioned in openings 436 on the ball coupler 432 and engage with openings 438 on the jaw closure shaft 430. A horizontal portion of a slide 440 extends along a top surface of the proximal handle portion 410 and is configured to slide distally and proximally along one or more slide points 441. A vertical portion at a proximal end of the slide 440 extends around the jaw closure shaft 430 and the ball coupler 432 in a cylindrical shape. The cylindrical end of the slide 440 is configured to apply a radially-inward compression force on the balls 434 to keep the balls 434 engaged with the openings 438 on the jaw closure shaft 438. Because the balls 434 also pass through the openings 436 on the ball coupler 432, the ball coupler 432 is configured to be fixedly coupled to the jaw closure shaft 430 as long as the compression force keeps the balls 434 engaged with the openings 438 on the jaw closure tube 430. A spring 418 is coupled between a distal wall of the proximal handle portion 410 and a distal end of the slide 440 and acts to bias the slide 440 proximally, toward a disengaged position in which the ball coupler 432 and the jaw closure shaft 430 are decoupled. A spring 444 is coupled between the slide 440 and the ball coupler 432 to prevent the slide 440 from moving too far in a proximal direction, however. Tabs 415 formed on the proximal end of the rotator 414 act to engage the rotator 414 to the proximal handle portion 410 because the tabs 415 engage a clip 442. The clip 442 extends externally from the proximal handle portion 410 to be accessible on a top surface of the proximal handle portion 410 and is engages a rod 440r that is part of the slide 440. A head 440h is formed on a distal end of the rod 440r, while a proximal end of the rod 440r couples to the slide 440. The head 440h is configured to prevent the rod 440r from moving proximally while the rod 440r is engaged with the clip 442 by passing the rod 440r through a keyhole 442k in the clip 442, as can be seen in FIG. 8, and the spring 418 is held in a compressed state when the rod 440r is engaged with the clip 442. As noted above, the clip 442 engages the tabs 415 to hold the rotator 414 and the shaft portion 412 on the proximal handle portion 410. The clip 442 is configured to be removable upwards from the proximal handle portion 410 by gripping the bulb 442b on the clip 442.

When the device is under a normal operation, the clip 442 engages the tabs 415 and the rod 440r. The tabs 415 keep the rotator 414 and the shaft portion 412 engaged with the proximal handle 410. The spring 418 is under compression, and the slide 440 is kept in a distal position by the clip 442 engaging the rod 440r. The slide 440 keeps the ball coupler 432 engaged with the jaw closure shaft 430 through interaction of the balls 434. The jaws can be opened and closed upon operation of the closure grip 420 using various techniques known in the art. Actuation of the firing actuator 424 sends a signal to the processor, which drives the motor 448 by providing power to the motor 448 from the power source. The motor 448 drives the gear box 452, which drives the motor bevel gear 454, which drives the drive bevel gear 456. The drive bevel gear 456 will rotate, causing the drive shaft 458 to advance and retract with the cutting assembly.

If a bailout operation of the cutting assembly is required, the clip 442 can be removed from the proximal handle portion 410. The clip 442 disengages from the tabs 415 and from the rod 440r. Disengaging the tabs 415 results in the shaft portion 412 and the rotator 414 being free to move distally away from and separate from the proximal handle portion 410. Disengaging from the rod 440r allows proximal motion of the slide 440 because the spring 418 is freed to expand proximally, forcing the slide 440 to move proximally relative to the ball coupler 432. Proximal motion of the slide 440 allows the balls 434 to move radially outward and disengage from the jaw closure shaft 430, releasing the balls 434 freely into the proximal handle portion 410 and releasing the jaw closure shaft 430 such that the jaws are freely openable and closable and can no longer be opened or closed upon operation of the closure grip 420. The drive shaft 458 with the cutting assembly is still engaged with the proximal handle portion 410. The shaft portion 412 with the rotator 414 can be withdrawn distally from the handle, while the drive shaft 458 remains engaged with the handle. As a result, the cutting assembly is pulled proximally relative to the jaws during distal removal of the shaft portion 412 from the proximal handle portion 410. With the cutting assembly removed from the jaws, the jaws are free to open.

The surgical device 400 cannot be reused after removing the clip 442 and retracting the cutting assembly. In other variations, the device can be reusable by re-engaging the clip with the rod and the tabs and thus by re-engaging the shaft portion with the proximal body portion by reinserting the clip. In such an example, the balls could be configured to move out of engagement with the jaw closure shaft while still engaging the ball coupler, for example by positioning detents on the slider to engage and retain the balls, allowing the device to be reset to normal operation upon moving the slide distally to recompress the spring before reengaging the clip with the rod and realigning the jaw closure shaft with the ball coupler. In such an example, a handle or lever could extend externally from the proximal body portion and be coupled to the slide to allow distal movement of the slide to recompress the spring. In this embodiment, the balls 434 and the ball coupler 432 are used to mate the jaw closure shaft 430 with the proximal handle portion 410, but any coupling mechanism can be used, such as a clip, a hook, etc.

Figure 9:
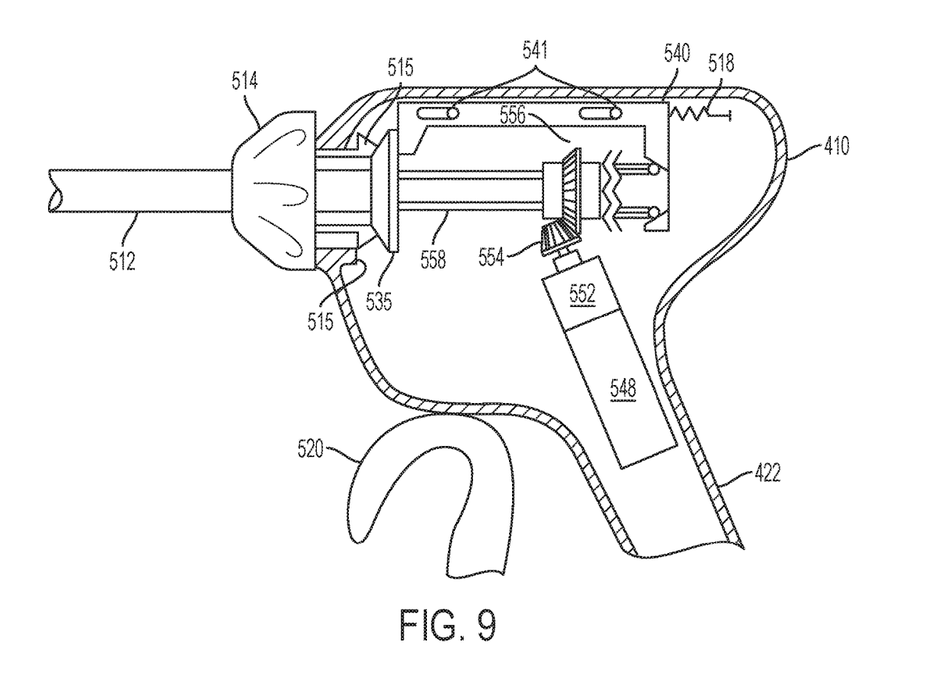
FIG. 9 is a side, partially cutaway view of another embodiment of a powered surgical device.
Figure 10:
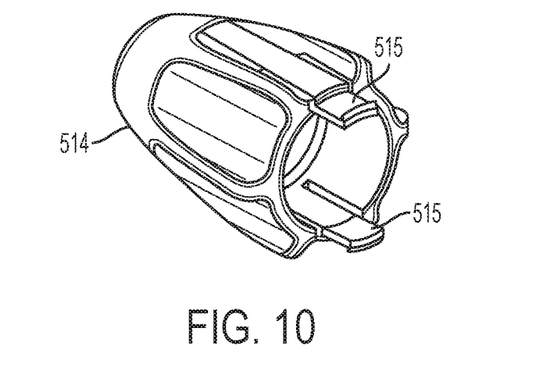
FIG. 10 is a perspective view of an embodiment of a rotator from the surgical device of FIG. 9.
Figure 11:
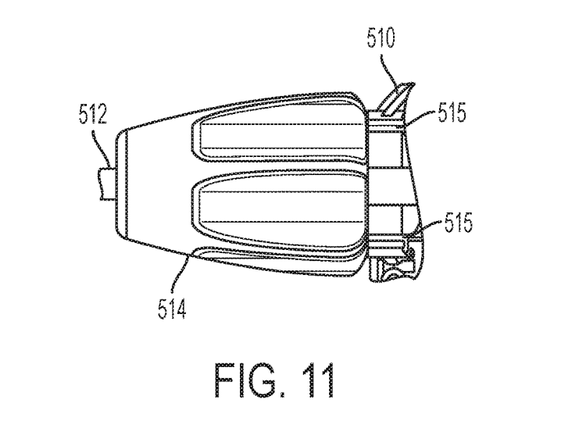
FIG. 11 is a side view of an embodiment of a rotator from the surgical device of FIG. 9.
Figure 12:
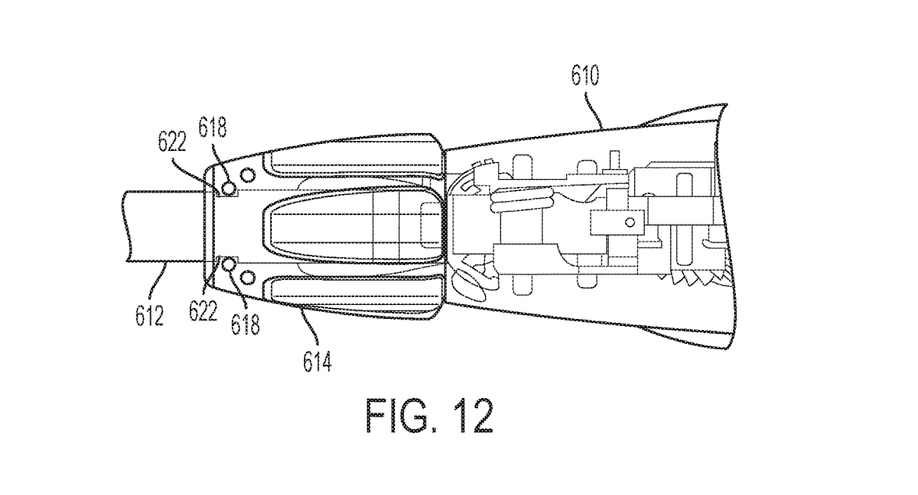
FIG. 12 is a side, partially cutaway, partially frame view of another embodiment of a powered surgical device.

FIGS. 9-11 illustrate another embodiment of a surgical device 500 having a bailout mechanism. The surgical device 500 can generally be configured and used similar to the surgical devices 100, 200 of FIGS. 1-4. Surgical device 500 has a proximal handle portion 510 including a stationary grip 522. The surgical device 500 has a shaft portion 512 coupled to a rotator 514, a closure grip 520, and a firing actuator 524 that can be configured to advance distally and/or retract proximally a cutting assembly through an end effector (not shown) positioned on a distal end of the shaft portion 512. The closure grip 520 is effective to move jaws of the end effector between open and closed positions using techniques known in the art. The firing actuator 524 is connected to and in communication with a processor (not shown) within the proximal handle portion 510. The processor is in communication with a motor 548 and a power source (not shown) such as a battery. The motor 548 is operably coupled to a gear box 552 and is disposed in the proximal handle portion 510. The motor 548 and the gear box 552 are operatively coupled to a motor bevel gear 554 that is operably coupled to a drive bevel gear 556, which in turn is operably coupled to a drive shaft 558.

Figure 9A:
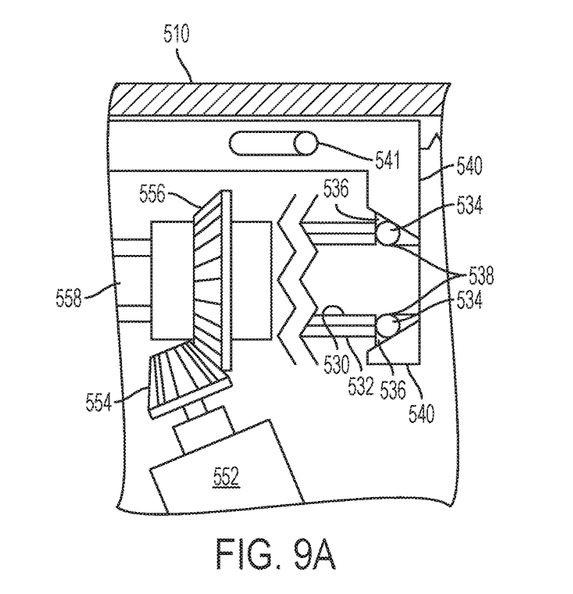
FIG. 9A is an enlarged side, partially cutaway view of part of the power surgical device of FIG. 9.

In this embodiment, a jaw closure shaft 530, which operates to open and close the jaws on the distal end of the shaft portion 512, engages with a ball coupler 532 and balls 534 (as seen in FIG. 9A). The jaw closure shaft 530 extends with the drive shaft 558 through the shaft portion 512. The ball coupler 532 surrounds the jaw closure shaft 530 and is coupled to the proximal handle portion 510. The ball coupler 532 engages the jaw closure shaft 530 via the balls 534. The balls 534 are positioned in openings 536 on the ball coupler 532 and engage with openings 538 on the jaw closure shaft 530. A horizontal portion of a slide 540 extends along a top surface of the proximal handle portion 510 and is configured to slide distally and proximally along one or more slide points 541. A vertical portion at a proximal end of the slide 540 extends around the jaw closure shaft 530 and the ball coupler 532 in the form of a cylinder. The cylindrical end of the slide 540 is configured to apply a radially-inward compression force on the balls 534 to keep the balls 534 engaged with the openings 538 on the jaw closure shaft 538. Because the balls 534 also pass through the openings 536 on the ball coupler 532, the ball coupler 532 is configured to mate to the jaw closure shaft 530 as long as compression force keeps the balls 534 engaged with the openings 538 on the jaw closure tube 530. A spring 518 is coupled between a proximal wall of the proximal handle portion 510 and a proximal end of the slide 540 and acts to bias the slide 540 distally into a position in which the ball coupler 532 and the jaw closure shaft 530 are engaged. Living flanges 515 extend proximally from the rotator 514 and act to maintain the rotator 514 in engagement with the proximal handle portion 510. A conical disc 535 extends around the drive shaft 558 and is slidable in a distal or proximal direction. The conical disc 535 is positioned between the living flanges 515 and the slide 540. The conical disc 535 can contact the living hinges 515 and the slide 540 but will not apply any force while the conical disc 535 is at rest.

When the device is under a normal operation, the living flanges 515 keep the rotator 514 and the shaft portion 512 mated to the proximal handle 510. The spring 518 biases the slide 540 to the distal position so that the slide 540 keeps the ball coupler 532 engaged with the jaw closure shaft 530 through interaction of the balls 534. The jaws can be opened and closed upon operation of the closure grip 520. The conical disc 535 is positioned between the living flanges 515 and the slide 540 and does not affect operation of the device 500. Actuation of the firing actuator 524 sends a signal to the processor, which drives the motor 548 by providing power to the motor 548 from the power source. The motor 548 drives the gear box 552, which drives the motor bevel gear 554, which drives the drive bevel gear 556 that drives the drive shaft 558 to advance and retract the cutting assembly.

If a bailout operation of the cutting assembly is required, the living flanges 515 can be depressed, disengaging the living flanges 515 from the proximal handle portion 510. As shown in FIG. 10, the living flanges 515 extend along an external surface on opposed sides of the rotator 514, allowing a user to grasp and depress the flanges 515. Disengaging the living flanges 515 releases the rotator 514, and thus from the proximal handle portion 510. Upon depressing the living flanges 515, a proximal end of each living flange 515 contacts the conical disc 535 and forces the conical disc 535 to move proximally. Proximal movement of the conical disc 535 forces the slide 540 proximally to overcome the spring bias of the spring 518. Proximal movement of the slide 540 relative to the ball coupler 532 allows the balls 534 to move radially outward and disengage from the jaw closure shaft 530, releasing the balls 534 freely into the proximal handle portion 510. Disengagement of the jaw closure shaft 530 allows the jaws to be freely openable and closable and to no longer be opened or closed upon operation of the closure grip 520. The drive shaft 558 with the cutting assembly is still engaged with the proximal handle portion 510. The shaft portion 512 with the rotator 514 can be withdrawn distally from the proximal handle portion 510, while the drive shaft 558 remains engaged with the proximal handle portion 510. As a result, the cutting assembly is pulled proximally relative to the jaws during distal removal of the shaft portion 512 from the proximal handle portion 510. With the cutting assembly removed from the jaws, the jaws are free to open.

The surgical device 500 cannot be reused after depressing the living flanges 515 and retracting the cutting assembly. In other variations, the device can be reusable by re-engaging the living flanges with the proximal handle portion. In such an example, the balls could be configured to move out of engagement with the jaw closure shaft while still engaging the ball coupler, for example by positioning detents on the slider to engage and retain the balls, allowing the device to be reset to normal operation upon realigning the jaw closure shaft with the ball coupler. In this embodiment, the balls 534 and the ball coupler 532 are used to engage the jaw closure shaft 530 with the proximal handle portion 510, but any coupling mechanism can be used, such as a clip, a hook, etc.

Figure 13:
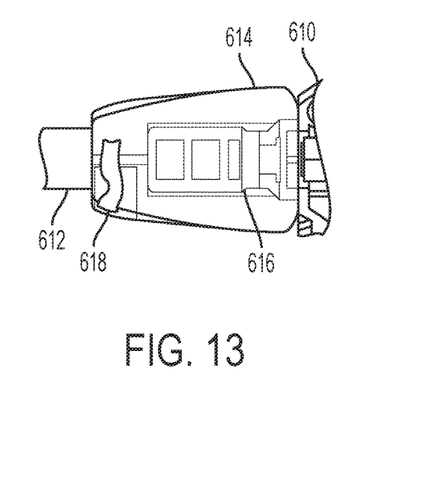
FIG. 13 is a side, partially cutaway view of the powered surgical device of FIG. 12.
Figure 14:
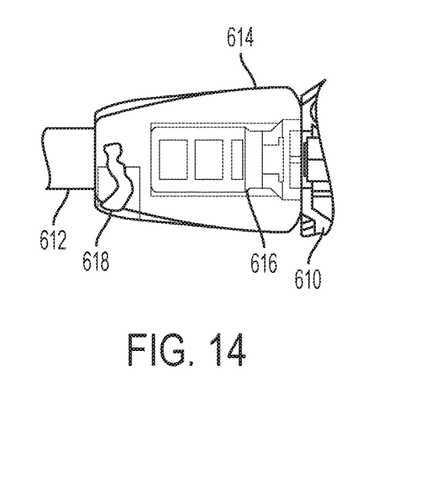
FIG. 14 is another side, partially cutaway view of the powered surgical device of FIG. 12.
Figure 15:
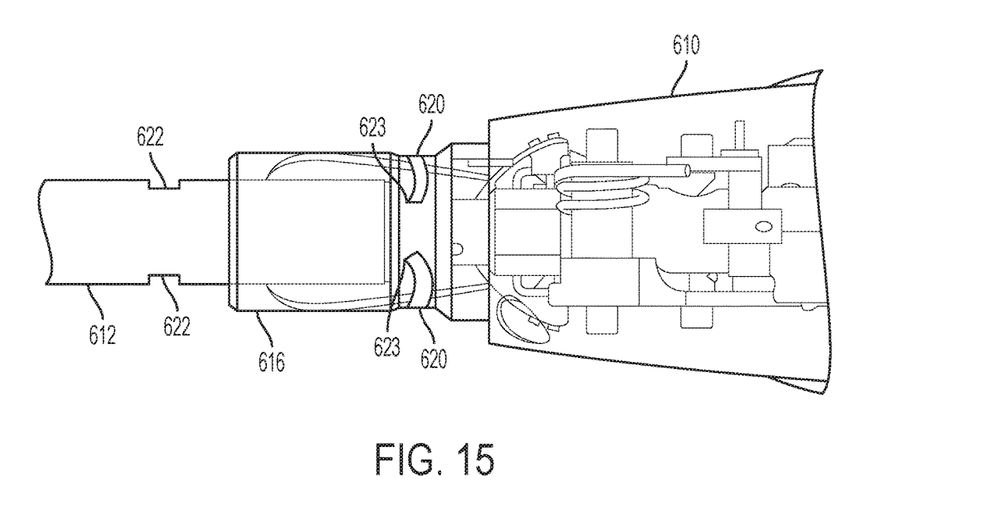
FIG. 15 is another side, partially cutaway view of the powered surgical device of FIG. 12.

Alternative mechanisms for disengaging the rotator and the shaft portion from the proximal handle portion are possible while remaining components of a surgical device are identical to those in FIG. 9. For example as seen in FIGS. 12-15, a rotator 614 engages a shaft portion 612 with a shroud 616 enclosed therein, and the shroud 616 engages the shaft portion 612. The shroud 616 forms an outer casing of the proximal handle portion 610 similar to the proximal handle portion 510 in FIG. 9. One or more living hinges 618 on the rotator 614 act to engage notches 622 on the shaft portion 612 to mate the rotator 614 to the shaft portion 612, while one or more living hinges 620 on the shroud 616 engage notches 623 on the shaft portion 612 to mate the shroud 616 to the shaft portion 612. Depressing the living hinges 618 on the rotator 614 disengages the rotator 614 from the shaft portion 612, as seen in FIGS. 13-14 as the living hinge 618 is depressed. The rotator 614 is then freely slidable distally along the shaft portion 612. After the rotator 614 is slid distally along the shaft portion 612, the shroud 616 is exposed. The living hinges 620 on the shroud 616 can then be depressed and disengage the shaft portion 612 from the shroud 616 of the proximal handle portion 610. A jaw closure shaft is then disengaged from the proximal handle portion 610 through a variety of coupling mechanisms, such as balls and a ball coupler similar to the embodiments described above or through other coupling mechanisms, such as a clip, a hook, etc. After the jaw closure shaft is disengaged, the shaft portion 612 can be withdrawn distally, causing a drive shaft, which is mated to the proximal handle portion, to retract the cutting assembly similar to the prior embodiments.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, components of the invention described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

Typically, the device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. Pub. No. 2009/0202387 filed Feb. 8, 2008 and entitled "System And Method Of Sterilizing An Implantable Medical Device," incorporated herein by reference in its entirety. It is preferred that device, if implanted, is hermetically sealed. This can be done by any number of ways known to those skilled in the art.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical device, comprising:
an elongate shaft assembly comprising,
 an elongate shaft having first and second jaws coupled to a distal end thereof for engaging tissue, and
 a cutting assembly extending through the elongate shaft for cutting tissue engaged between the first and second jaws; and
a handle having a motorized gear assembly coupled to a drive shaft for causing movement of the drive shaft, the handle including a mechanism for detaching the elongate shaft from the handle such that the elongated shaft can be withdrawn distally from the handle to cause the drive shaft to proximally retract the cutting assembly from the first and second jaws.

2. The device of claim 1, wherein the device includes at least one living hinge that can be depressed to at least partially detach the elongate shaft.

3. The device of claim 1, wherein the handle includes a button that, when actuated, allows the elongate shaft to be at least partially detached from the handle.

4. The device of claim 1, wherein the elongated shaft assembly is coupled to the handle by a bailout clip removably disposed in the handle, wherein removal of the bailout clip allows the elongate shaft assembly to be at least partially detached from the handle.

5. The device of claim 1, wherein the elongate shaft assembly includes a jaw closure shaft configured to move the first and second jaws between an opened position and a closed position, the jaw closure shaft being coupled to the handle by a plurality of balls, and the balls being configured to disengage from the jaw closure shaft to allow the jaw closure shaft to detach from the handle.

6. The device of claim 5, wherein the device includes at least one living hinge that can be depressed to at least partially detach the elongate shaft.

7. The device of claim 5, wherein the handle includes a button that, when actuated, allows the elongate shaft assembly to be at least partially detached from the handle.

8. The device of claim 5, wherein the elongated shaft assembly is coupled to the handle by a bailout clip removably disposed in the handle, wherein removal of the bailout clip allows the elongate shaft assembly to be at least partially detached from the handle.

9. The device of claim 1, further comprising a slide having a horizontal portion that extends along a top surface of the handle and a vertical portion that extends around a jaw closure shaft positioned within the handle.

10. A surgical device, comprising:
a handle;
an elongate shaft assembly extending distally therefrom, the elongate shaft assembly having first and second jaws at a distal end thereof for engaging tissue therebetween;
a cutting assembly movable relative to the first and second jaws so as to cut tissue engaged between the first and second jaws;
a drive shaft extending from the handle through the elongate shaft assembly and being coupled to the cutting assembly for moving the cutting assembly relative to the first and second jaws; and
a motorized gear assembly coupled to the drive shaft and configured to cause movement of the drive shaft;
wherein the elongate shaft assembly is at least partially detachable from the handle such that, when detached, the drive shaft can be manually retracted in a proximal direction relative to the elongate shaft to move the cutting assembly relative to the first and second jaws.

11. The device of claim 10, wherein the device includes at least one living hinge that can be depressed to at least partially detach the elongate shaft assembly.

12. The device of claim 10, wherein the handle includes a button that, when activated, allows the elongate shaft assembly to be at least partially detached from the handle.

13. The device of claim 10, wherein the elongate shaft assembly is coupled to the handle by a bailout clip removably disposed in the handle, wherein removal of the bailout clip allowing the elongate shaft assembly to be at least partially detached from the handle.

14. The device of claim 10, wherein the elongate shaft assembly includes a jaw closure shaft configured to move the first and second jaws between an opened position and a closed position, the jaw closure shaft being coupled to the handle by a plurality of balls, and the balls being configured to disengage from the jaw closure shaft to allow the jaw closure shaft to detach from the handle.

15. The device of claim 14, wherein the device includes at least one living hinge that can be depressed to at least partially detach the elongate shaft assembly.

16. The device of claim 14, wherein the handle includes a button that, when activated, allows the elongate shaft assembly to be at least partially detached from the handle.

17. The device of claim 14, wherein the elongate shaft assembly is coupled to the handle by a bailout clip removably disposed in the handle, wherein removal of the bailout clip allowing the elongate shaft assembly to be at least partially detached from the handle.

18. The device of claim 10, further comprising a slide having a horizontal portion that extends along a top surface of the handle and a vertical portion that extends around a jaw closure shaft positioned within the handle.

* * * * *